(12) United States Patent
Kim et al.

(10) Patent No.: US 11,657,907 B2
(45) Date of Patent: May 23, 2023

(54) METHOD FOR SETTING AUTHORITY FOR USE OF BRAIN STIMULATION DEVICE AND DEVICE IMPLEMENTING SAME

(71) Applicant: Y-BRAIN INC, Seongnam-si (KR)

(72) Inventors: Seong-Hoon Kim, Seongnam-si (KR); Ki-Won Lee, Seongnam-si (KR)

(73) Assignee: Y-BRAIN INC, Seongnam-si (KR)

( * ) Notice: Subject to any disclaimer, the term of this patent is extended or adjusted under 35 U.S.C. 154(b) by 554 days.

(21) Appl. No.: 16/643,699

(22) PCT Filed: Aug. 8, 2018

(86) PCT No.: PCT/KR2018/009051
§ 371 (c)(1),
(2) Date: Mar. 2, 2020

(87) PCT Pub. No.: WO2019/045308
PCT Pub. Date: Mar. 7, 2019

(65) Prior Publication Data
US 2020/0202998 A1 Jun. 25, 2020

(30) Foreign Application Priority Data
Aug. 30, 2017 (KR) .................. 10-2017-0110197

(51) Int. Cl.
*G16H 20/70* (2018.01)
*G16H 20/30* (2018.01)
(Continued)

(52) U.S. Cl.
CPC ............... *G16H 20/70* (2018.01); *A61N 1/20* (2013.01); *G06Q 20/325* (2013.01);
(Continued)

(58) Field of Classification Search
CPC .......... G16H 20/70; G16H 20/30; A61N 1/20; G06Q 20/325; H04L 9/3213; H04L 63/08
See application file for complete search history.

(56) References Cited

U.S. PATENT DOCUMENTS 9,278,208 B1* 3/2016 Gilson ............... A61N 1/36067
2008/0183502 A1* 7/2008 Dicks ..................... G16H 40/67
705/2

(Continued)

FOREIGN PATENT DOCUMENTS

JP 2007-67782 A 3/2007
JP 2014-170458 A 9/2014
(Continued)

OTHER PUBLICATIONS

International Search Report dated Nov. 26, 2018, corresponding to International Application No. PCT/KR2018/009051.

*Primary Examiner* — John P Go
*Assistant Examiner* — Aaisha Abdullah
(74) *Attorney, Agent, or Firm* — Hauptman Ham, LLP

(57) ABSTRACT

Disclosed is a method for setting authority for use of a brain stimulation device and a device implementing the same, and the method for setting authority for use of a brain stimulation device according to the present disclosure comprises the steps in which: a communication unit of a personal communication device receives, from a server device, a time token for which the authority for use of the brain stimulation device is set; the communication unit transmits the time token to the brain stimulation device or the server device; and after a time corresponding to the usage time of the brain stimulation device stored in the time token has elapsed, the communication unit receives, from the brain stimulation device or the server device, a message to delete the time token or to change the value of a specific field of the time token.

7 Claims, 12 Drawing Sheets

(51) Int. Cl.
  *A61N 1/20* (2006.01)
  *G06Q 20/32* (2012.01)
  *H04L 9/32* (2006.01)
  *H04L 9/40* (2022.01)

(52) U.S. Cl.
  CPC .......... G16H 20/30 (2018.01); H04L 9/3213 (2013.01); H04L 63/08 (2013.01)

(56) References Cited

U.S. PATENT DOCUMENTS

| | | | | |
|---|---|---|---|---|
| 2008/0235805 | A1* | 9/2008 | Pfitzmann | G06F 21/105 |
| | | | | 726/27 |
| 2012/0065458 | A1* | 3/2012 | Tol | A61N 1/372 |
| | | | | 600/25 |
| 2014/0058189 | A1* | 2/2014 | Stubbeman | A61M 21/02 |
| | | | | 600/13 |
| 2015/0182410 | A1* | 7/2015 | Burris | A61K 31/4468 |
| | | | | 514/236.8 |
| 2016/0021687 | A1* | 1/2016 | Granbery | H04W 76/11 |
| | | | | 455/41.2 |
| 2016/0063471 | A1* | 3/2016 | Kobres | G06Q 20/40 |
| | | | | 705/18 |
| 2016/0283030 | A1* | 9/2016 | Won | G06F 3/1431 |
| 2016/0299779 | A1* | 10/2016 | Kulkarni | H04W 4/90 |
| 2016/0306955 | A1* | 10/2016 | Martin | G06F 21/34 |
| 2017/0012951 | A1* | 1/2017 | Mennes | H04L 63/10 |
| 2017/0063824 | A1 | 3/2017 | Li et al. | |
| 2017/0080256 | A1* | 3/2017 | Kim | A61B 5/4836 |
| 2017/0119276 | A1* | 5/2017 | Lee | A61B 5/112 |
| 2017/0185103 | A1* | 6/2017 | Kim | G06V 10/143 |
| 2017/0372288 | A1* | 12/2017 | Li | H01R 24/28 |

FOREIGN PATENT DOCUMENTS

| | | |
|---|---|---|
| KR | 10-1284892 B1 | 8/2013 |
| KR | 10-1465587 B1 | 11/2014 |
| KR | 2015-0030224 A | 3/2015 |
| KR | 10-1592178 B1 | 2/2016 |
| KR | 10-1659708 B1 | 9/2016 |

* cited by examiner

FIG. 3

Table 51:

| usage_id | user_id | start_date_time | end_date_time | machine_id | usage_min | usage_mode | price |
|---|---|---|---|---|---|---|---|
| usage005 | user0001 | 2017.04.28 15:00:00 | 2017.05.05 15:00:00 | mac0010 | 20 | alpha_2 | 30000 |
| usage006 | user0001 | 2017.05.05 15:00:00 | 2017.05.12 15:00:00 | mac0010 | 15 | alpha_1 | 25000 |
| usage007 | user0001 | 2017.05.12 15:00:00 | 2017.05.19 15:00:00 | mac0025 | 15 | beta_1 | 28000 |

Table 52:

| usage_id | start_date_time | end_date_time | machine_id | usage_coun | usage_min | usage_mode | price |
|---|---|---|---|---|---|---|---|
| usage015 | 2017.04.28 15:00:00 | 2017.05.19 15:00:00 | mac0010 | 3 | 20 | alpha_2 | 90000 |

FIG. 4

Table 61:

| usage_id | start_date_time | end_date_time | machine_id | usage_min | usage_mode |
|---|---|---|---|---|---|
| usage005 | 2017.04.28 15:00:00 | 2017.05.05 15:00:00 | mac0010 | 20 | alpha_2 |
| usage006 | 2017.05.05 15:00:00 | 2017.05.12 15:00:00 | mac0010 | 15 | alpha_1 |
| usage007 | 2017.05.12 15:00:00 | 2017.05.19 15:00:00 | mac0025 | 15 | beta_1 |

Table 62:

| usage_id | start_date_time | end_date_time | machine_id | usage_coun | usage_min | usage_mode |
|---|---|---|---|---|---|---|
| usage015 | 2017.04.28 15:00:00 | 2017.05.19 15:00:00 | mac0010 | 3 | 20 | alpha_2 |

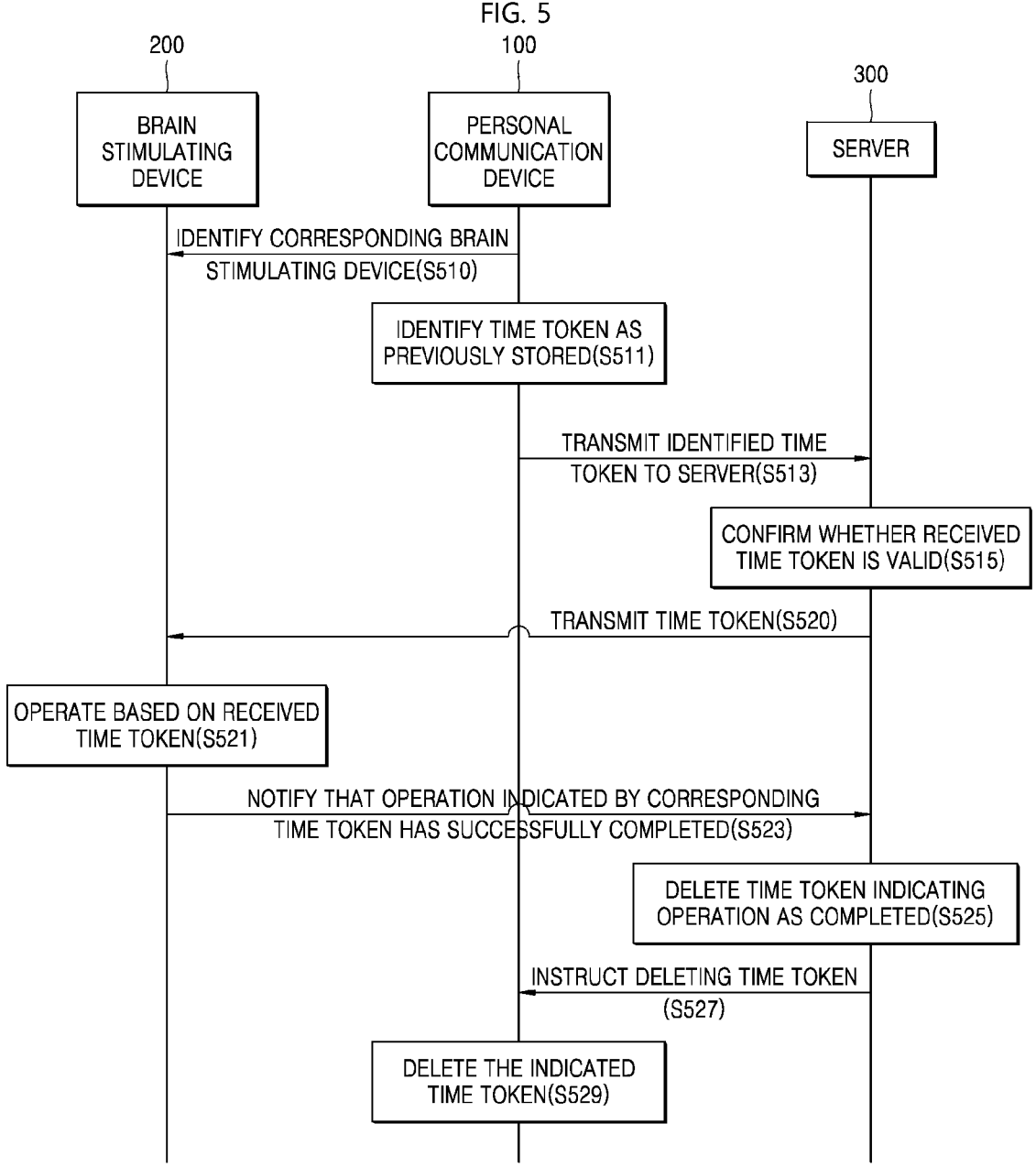

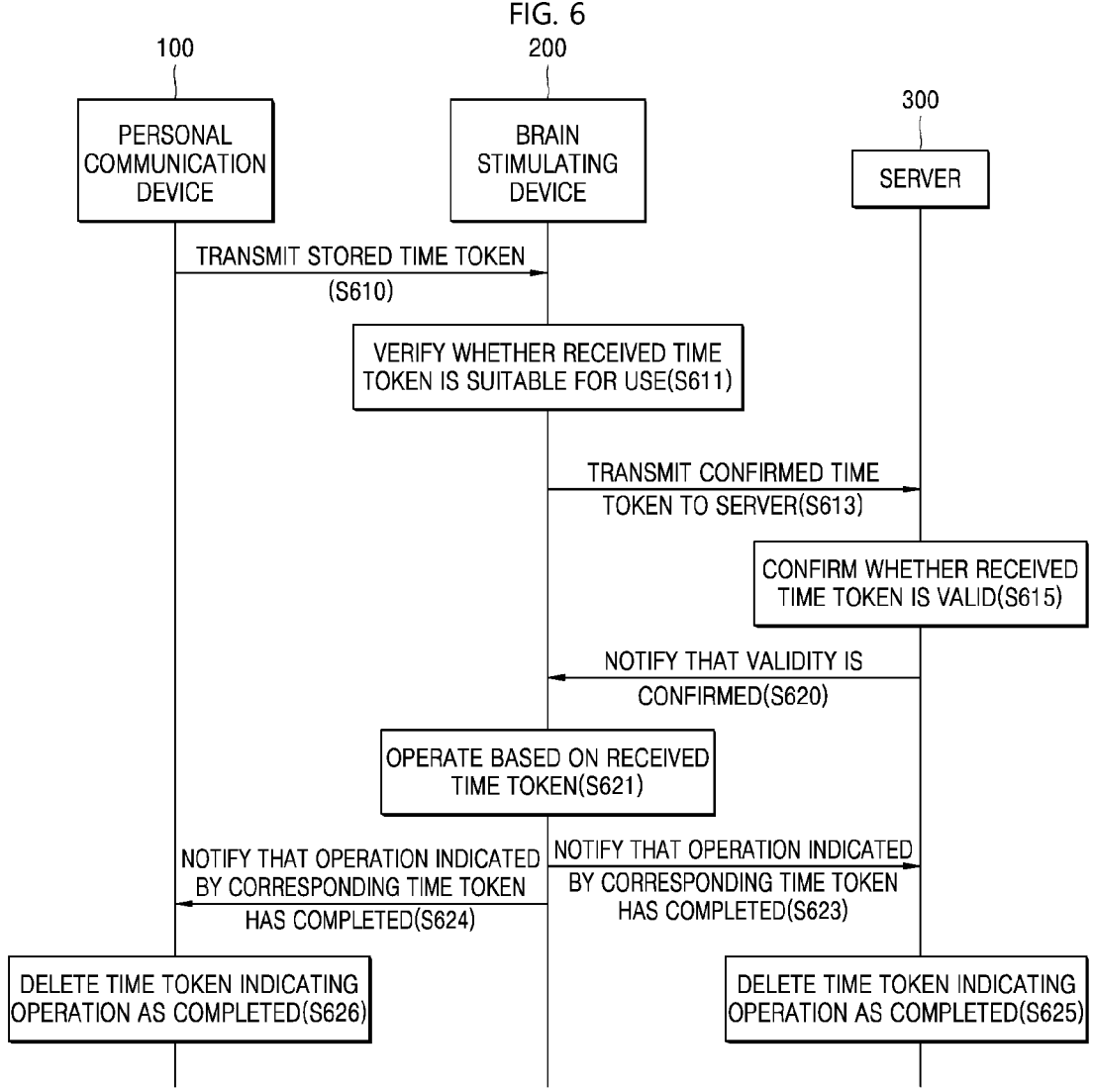

| usage_id | user_id | start_date_time | end_date_time | machine_id | usage_min | usage_mode | price |
|---|---|---|---|---|---|---|---|
| usage005 | user0001 | 2017.04.28 15:00:00 | 2017.05.05 15:00:00 | mac0010 | 20 | alpha_2 | USE COMPLETED |
| usage006 | user0001 | 2017.05.05 15:00:00 | 2017.05.12 15:00:00 | mac0010 | 15 | alpha_1 | 25000 |
| usage007 | user0001 | 2017.05.12 15:00:00 | 2017.05.19 15:00:00 | mac0025 | 15 | beta_1 | 28000 |

72:

| usage_id | user_id | start_date_time | end_date_time | machine_id | usage_min | usage_mode | price |
|---|---|---|---|---|---|---|---|
| usage005 | user0001 | 2017.04.28 15:00:00 | 2017.05.05 15:00:00 | mac0010 | 20 | alpha_2 | USE COMPLETED |
| usage006 | user0001 | 2017.05.05 15:00:00 | 2017.05.12 15:00:00 | mac0010 | 15 | alpha_1 | 25000 →2300 |
| usage007 | user0001 | 2017.05.12 15:00:00 | 2017.05.19 15:00:00 | mac0025 | 15 | beta_1 | 28000 |

73:

| usage_id | user_id | start_date_time | end_date_time | machine_id | usage_min | usage_mode | price |
|---|---|---|---|---|---|---|---|
| usage005 | user0001 | 2017.04.28 15:00:00 | 2017.05.05 15:00:00 | mac0010 | 20 | alpha_2 | USE COMPLETED |
| usage006 | user0001 | 2017.05.05 15:00:00 | 2017.05.12 15:00:00 | mac0010 | 15 | alpha_1 →alpha_2 | 25000 →2300 |
| usage007 | user0001 | 2017.05.12 15:00:00 | 2017.05.19 15:00:00 | mac0025 | 15 | beta_1 | 28000 |

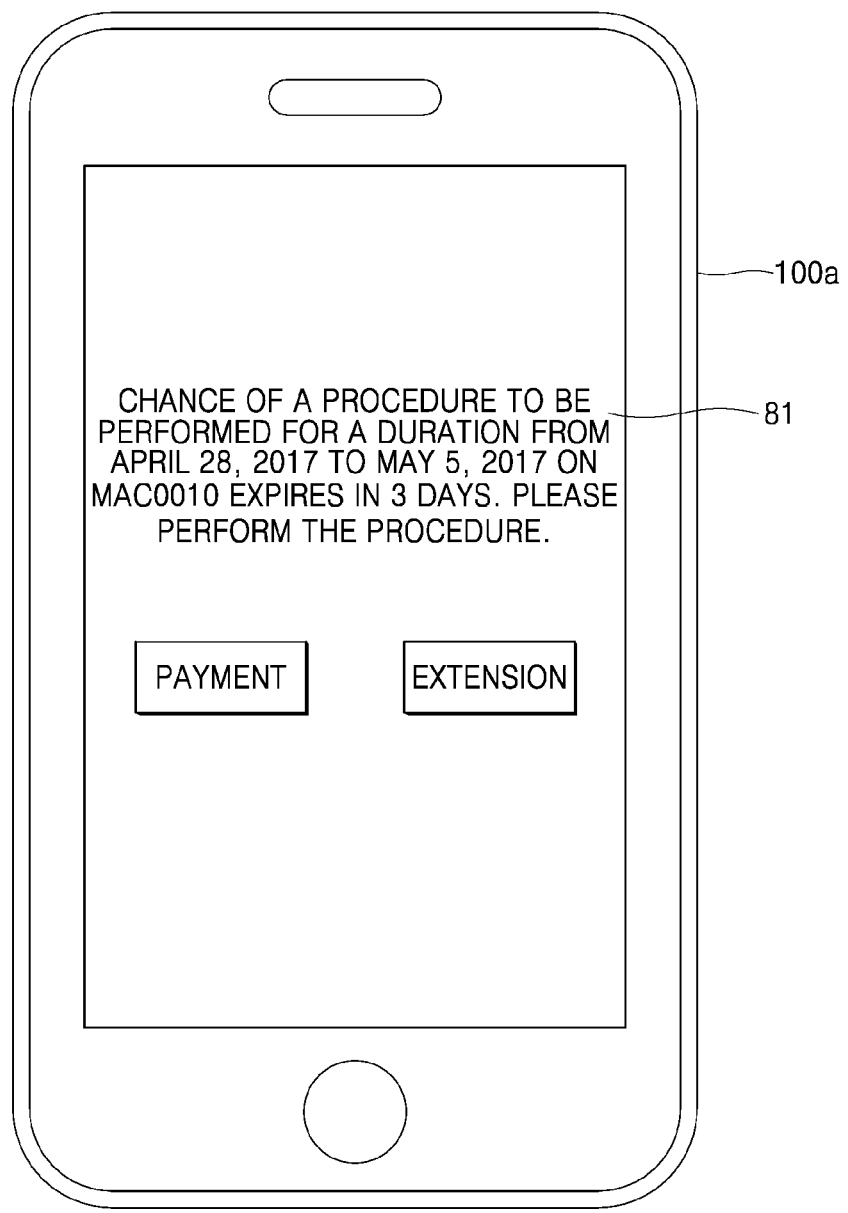

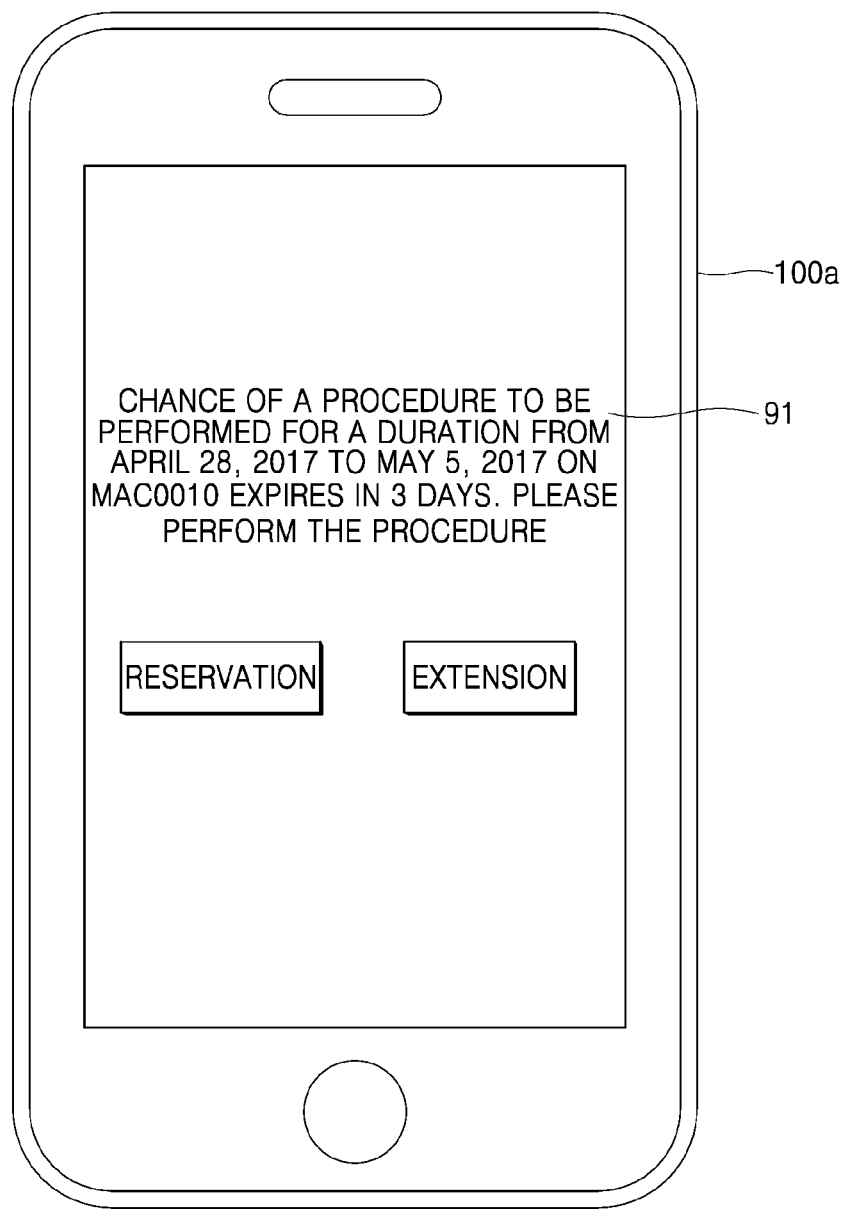

METHOD FOR SETTING AUTHORITY FOR USE OF BRAIN STIMULATION DEVICE AND DEVICE IMPLEMENTING SAME

CROSS-REFERENCE TO RELATED APPLICATIONS

This application is the National Phase of PCT International Application No. PCT/KR2018/009051 filed on Aug. 8, 2018, and claims priority benefit under 35 U.S.C. § 119(a) to Patent Application No. 10-2017-0110197, filed in the Republic of Korea on Aug. 30, 2017, all of which are hereby expressly incorporated by reference into the present application.

TECHNICAL FIELD

The present disclosure relates to a method for configuring a usage authorization of a brain stimulating device, and to a device implementing the same. More specifically, the present disclosure relates to a method for configuring a usage authorization so that a brain stimulating device may be used on a user basis and to an authority configuration device that implements the method.

BACKGROUND ART

A brain is an internal organ of a human head and is the highest central organ of a nervous system and is divided into a cerebral, a cerebellum, a middle brain, a leg brain, and a medulla. Further, the brain produces a brain wave as a signal obtained by measuring a sum of neuronal activity levels of the brain at the brain's epidermis.

A method of measuring a state of the brain may include a brain wave (EEG) test in which a pad with an electrode is mounted on a scalp to measure the brain wave received from the electrode. Alternatively, the method may include a CT scan in which the brain is imaged in a tomography manner at various angles using radiation or ultrasound, or a MRI scan in which the brain is imaged in a tomography manner at various angles using magnetic resonance.

Various concepts are known in a field of neural stimulation of brain structures. A brain stimulation which stimulates the brain to achieve a predefined purpose is largely classified as invasive brain stimulation and non-invasive brain stimulation. The invasive brain stimulation refers to a method of penetrating an electrode into the brain via surgery and applying an electrical signal thereto, which requires a medical procedure by a surgeon.

On the other hand, the non-invasive brain stimulation refers to a method of stimulating the brain without invading the electrode into a skull of the user to achieve a predetermined effect. This method stimulates the brain using electricity or magnetism. The non-invasive brain stimulation may perform stimulation without a medical procedure by a surgeon. Thus, the non-invasive brain stimulation may be directly performed by a user to achieve easiness of the performance compared to the invasive brain stimulation.

The non-invasive brain stimulation may apply the stimulation to the brain, and therefore requires use safety. For the safety of use, it is necessary to limit the number of use times of a brain stimulation device based on a duration such that one user may use the device, for example, once a day or twice a day. That is, in order to configure a usage authorization for each user and to control a procedure when two or more users share one brain stimulating device, it is necessary to configure a use frequency or authority for each user. Thus, the disclosure is directed to an authority configuration method for configuring the usage authorization of the brain stimulating device for a user, and a device implementing the method.

Disclosure

Technical Purposes

A purpose of the present disclosure is to provide a method and system for configuring a usage authorization of a brain stimulating device for a user based on a time token.

Another purpose of the present disclosure is to provide a method and system for configuring a usage authorization of a brain stimulating device in which the usage authorization of the brain stimulating device is pre-allocated to a communication device of a user so that the brain stimulating device to be used by many users may be safely operated based on an user identification.

Purposes disclosed in the present disclosure are not limited to the purposes as mentioned above. Other purposes as not mentioned above will be clearly understood by those skilled in the art from following descriptions.

Technical Solutions

In one embodiment of the present disclosure, a method for configuring a usage authorization of a brain stimulating device may include transmitting, by a communicator of a personal communication device, identification information of a user to a server; receiving, by the communicator, a time token having a usage authorization of a brain stimulating device configured therein, from the server, and, storing, by the communicator, the time token in a storage of the personal communication device; identifying, by the communicator, a brain stimulating device adjacent thereto, and transmitting the stored time token to the brain stimulating device or the server; after a time duration corresponding to a use time duration of the brain stimulating device stored in the time token has lapsed, receiving, by the communicator, a message from the brain stimulating device or the server, wherein the message instructs deleting the time token or changing a value of a specific field of the time token to deactivate the time token; and deactivating or deleting, by a controller of the personal communication device, the time token based on the received message.

In another embodiment of the present disclosure, a method for configuring a usage authorization of a brain stimulating device may include receiving, by a communicator of a server, identification information of a user from a personal communication device; generating, by a controller of the server, a time token having a usage authorization of the brain stimulating device configured therein based on the identification information, and storing, the controller, the time token in a storage of the server; transmitting, by the communicator, the time token to the personal communication device; receiving, by the communicator, the time token from the personal communication device or the brain stimulating device, and, identifying, by the controller, validity of the time token; receiving, by the communicator, a message from the brain stimulating device to notify that use of the brain stimulating device defined in the time token is completed; and deleting, by the controller, the time token stored in the storage or changing, by the controller, a value of a specific field of the time token to deactivate the time token.

In still another embodiment of the present disclosure, a brain stimulating device may include a brain stimulator configured to apply electrical or magnetic stimulation to a brain; a communicator configured to communicate with a server or a personal communication device to send or receive a message and a time tokens thereto and therefrom; and a controller configured to: control the brain stimulator based on a use time and a use mode defined in the time token; after the brain stimulator has operated for a use time duration defined in the time token, generate a message to instructs deleting the time token or changing a value of a specific field of the time token to deactivate the time token; and control the communicator to transmit the message to at least one of the server or the personal communication device.

Technical Effects

In accordance with the present disclosure, the method may configure the usage authorization of the brain stimulating device for the user based on the time token. Thus, the server, the personal communication device, and the brain stimulating device that implement the method may be provided.

In accordance with the present disclosure, the brain stimulating device may operate in a user-customized manner depending on the usage authorization and the user identification information.

Effects provided by the present disclosure are not limited to those as mentioned above. Other effects as not mentioned above will be clearly understood by those skilled in the art from the following descriptions.

BRIEF DESCRIPTION OF DRAWINGS

FIG. 3 shows usage information according to an embodiment of the present disclosure.

FIG. 4 shows a configuration of a time token according to an embodiment of the present disclosure.

FIG. 5 illustrates a process of using a brain stimulating device 200 using a time token according to an embodiment of the present disclosure.

FIG. 6 shows a process of using the brain stimulating device 200 using a time token according to another embodiment of the present disclosure.

FIG. 7 shows that usage information is updated after operation of a brain stimulating device according to an embodiment of the present disclosure.

FIG. 8 illustrates a notification message of a personal communication device according to an embodiment of the present disclosure.

FIG. 9 shows a notification message of a personal communication device according to another embodiment of the present disclosure.

DETAILED DESCRIPTIONS

Figure 1:
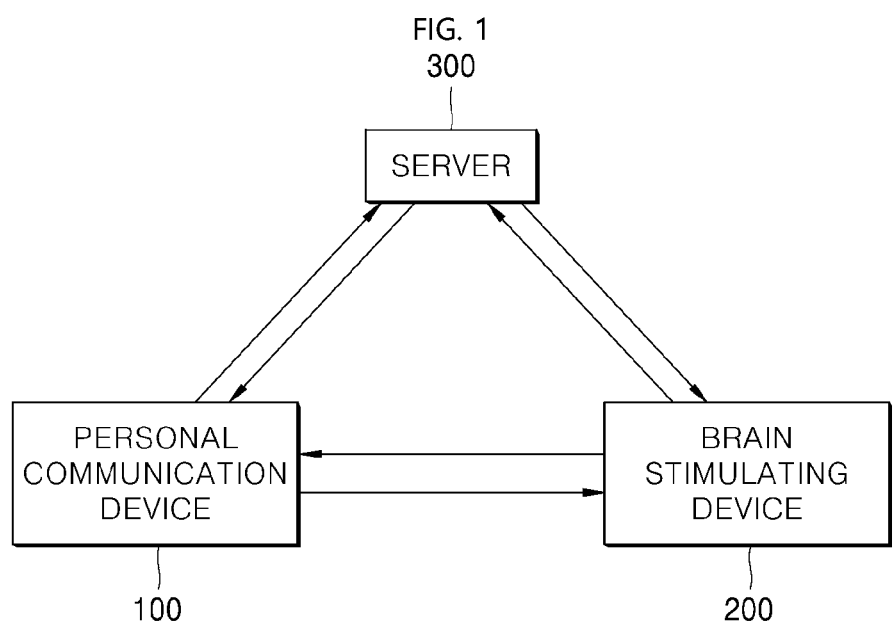
FIG. 1 shows a configuration of devices implementing a brain stimulating method for configuring a usage authorization according to an embodiment of the present disclosure.

Advantages and features of the present disclosure, and a method for achieving them will be apparent with reference to the embodiments as described below in detail in conjunction with the accompanying drawings. However, the present disclosure is not limited to the embodiments as disclosed below, but may be implemented in various forms. Only these embodiments are provided to ensure that the present disclosure is complete and are provided to fully inform the person of ordinary skill in the technical field to which the present disclosure belongs of a scope of the disclosure. The present disclosure is only defined by a scope of the claims. Like reference numerals refer to like elements throughout the disclosure.

In order to clarify the present disclosure, the present disclosure has omitted components not related to the description. Like reference numerals designate like or similar components throughout the specification. Further, the embodiments of the present disclosure will be described in detail with reference to exemplary drawings. In allocating reference numerals to components of each drawing respectively, the same component may have the same reference numeral even though the same component is displayed on different drawings. Further, well-known methods, procedures, and components have not been described in detail so as not to unnecessarily obscure aspects of the present disclosure.

It will be understood that, although the terms "first", "second", "third", A, B, (a), (b), and so on may be used herein to describe various elements, components, regions, layers and/or sections, these elements, components, regions, layers and/or sections should not be limited by these terms. These terms are used to distinguish one element, component, region, layer or section from another element, component, region, layer or section. It will be understood that when an element or layer is referred to as being "connected to", or "coupled to" another element or layer, it may be directly on, connected to, or coupled to the other element or layer, or one or more intervening elements or layers may be present. In addition, it will also be understood that when an element or layer is referred to as being "between" two elements or layers, it may be the only element or layer between the two elements or layers, or one or more intervening elements or layers may be present.

In an embodiment of the present disclosure, a process in which an usage authorization is configured using a device such as a computer, a smartphone, or a mobile such as an iPhone or a tablet, and, then, a request that an electrical stimulation device operates based on the configured authority is performed toward the electrical stimulation device, and, then, electrical stimulation is executed by the electrical stimulation device based on the configured authority will be provided.

In an embodiment of the present disclosure, examples of specific brain stimulations employed by the brain stimulating device may include DES (deep electrical stimulation), TMS (transcranial magnetic stimulation), TES (transcranial electrical stimulation), tDCS (transcranial direct current stimulation), and tRNS (transcranial random noise stimulation). However, the present disclosure is not limited to those specific stimulations. Various brain stimulating methods may be implemented in the present device.

FIG. 1 shows a configuration of devices implementing a brain stimulating method for configuring an usage authorization according to an embodiment of the present disclosure. The devices include a personal communication device 100, a brain stimulating device 200, and a server 300 that communicates therewith.

The personal communication device 100 refers to a device such as a smartphone, a smart watch, or a tablet computer capable of communicating with the external server 300 or the brain stimulating device 200. In a broad sense, the personal communication device 100 includes a device that a user may either personally possess or personally log in by entering her/his ID.

The brain stimulating device 200 refers to a device that is mounted on the user to provide electrical or magnetic stimulation to a brain of the user. In one embodiment, the brain stimulating device 200 may be a tDCS device employing the above-described transcranial direct current stimulation. In addition, various brain stimulation devices may be embodiments of the brain stimulating device 200. The brain stimulating device 200 may have a communicator that implements a separate communication function and may communicate with the personal communication device 100 and the server 300.

The server 300 may then communicate with the personal communication device 100. Further, the server 300 may communicate with the brain stimulating device 200.

The server 300 and the personal communication device 100 may share information for obtaining a usage authorization to use the brain stimulating device 200 for the user as described above. The information constituting the usage authorization necessary for the user to use the brain stimulating device 200 may include identification information USERID for identifying the user and a time token containing a use time and a number of use times of the brain stimulating device 200, or a timing when the brain stimulating device 200 is available. Thus, in one example, the time token may include a file having the usage authorization configured therein.

The identification information refers to information for identifying the user. After the user logs in to the server 300 using software installed on the personal communication device 100 or performs an authentication process, the identification information USERID of the user may be stored on the communication device 100.

The time token may be generated based on a timing when the brain stimulating device 200 is available, a timing when the user is available for use of the brain stimulating device 200, a payment corresponding to a use duration, a pre-assigned device use coupon, or prescription information on use of the brain stimulating device 200 issued by a medical staff.

Figure 2:
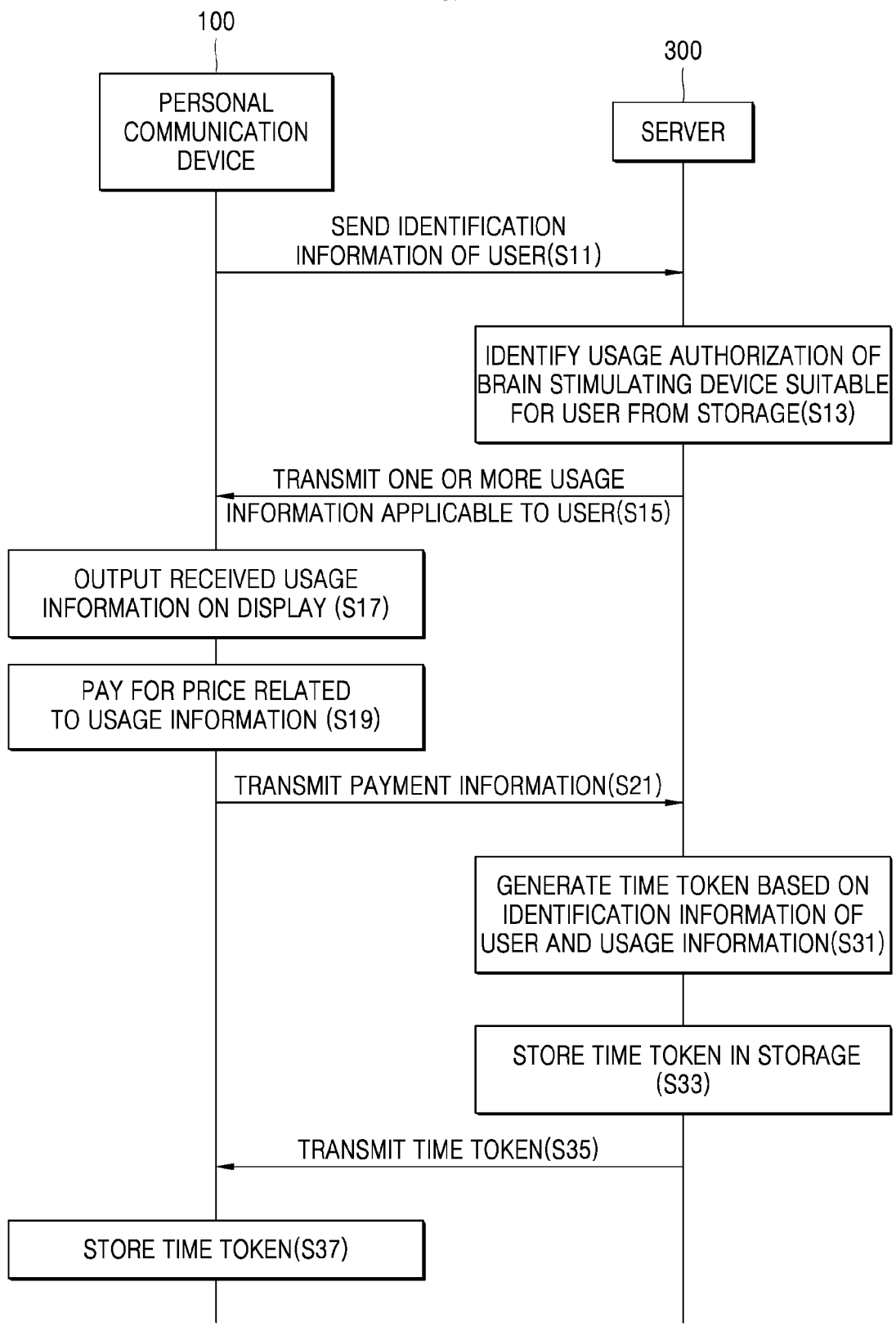
FIG. 2 shows a process of assigning an authority between a personal communication device 100 and a server 300 according to one embodiment of the present disclosure.

FIG. 2 shows a process of assigning a usage authorization between the personal communication device 100 and the server 300 according to one embodiment of the present disclosure.

The personal communication device 100 is in a state where an application is installed therein to communicate with the server 300. Accordingly, in one example, a process in which the personal communication device 100 communicates with the server 300 and configures information for prescription may be executed by the above-described application.

The personal communication device 100 sends the identification information USERID of the user to the server 300 S11. The server 300 identifies a usage authorization of the brain stimulating device 200 suitable for the user from a storage thereof using the identification information USERID of the user as a search key S13. In this connection, in one example, the usage authorization may include information whether the user has an authority to use the brain stimulating device 200, or if so, a function for the user to use. In one example, the server 300 may retrieve the information from a storage. One example of the storage may be database.

In more detail, usage information includes the identification information of the user, available duration information, detailed information, price, and the like. The available duration information may be information about a certain duration for which the user can use the brain stimulating device 200. The detailed information includes identification information about the brain stimulating device 200 to be used by the user, information about a time at which the user uses the brain stimulating device 200, and information about a function of the brain stimulating device 200 to be used by the user. Further, optionally, additional information such as location information and use duration of the brain stimulating device 200 may be included in the detailed information. Then, the server 300 transmits the above-described usage information, that is, one or more usage information applicable to the user S15. There may be a plurality of the usage information as transmitted in S15. N of the usage information (N is a natural number, and N>0) for the user may be transmitted in S15 for each duration. However, at least two usage information may be stored in a single message structure and thus may be transmitted at one time.

The personal communication device 100 outputs the received usage information on a display S17. In this connection, when one or more pieces of usage information are received, the personal communication device 100 first outputs usage information that takes precedence in terms of a time.

The user identifies usage information displayed in the personal communication device 100, and a price (or points, a coupon, etc.) required to use the brain stimulating device 200 based on the corresponding usage information, and then pays for the price for using the personal communication device 100 S19. Then, the payment information is sent to the server 300 S21. The payment information may include identification information about the usage information for which the payment is executed by the user.

Although not shown in the drawing, in another embodiment, another payment such as a card payment or a deposit payment may be performed without using the personal communication device 100, and then the payment information may be transmitted to the server 300.

Thereafter, the server 300 generates a time token based on the identification information of the user and the usage information as described above S31 and stores the time token in the storage S33, and, at the same time or subsequently, the server 300 sends the time token to the personal communication device 100 S35. In this process, the server 300 may transmit both of the time token and the user identification information to the personal communication device 100 or may transmit only the time token thereto. The personal communication device 100 stores therein the time token S37. Alternatively, the user identification information and the time token may be stored together in the personal communication device 100.

In FIG. 2, when the personal communication device 100 transmits the identification information of the user, the server 300 may restrict use of the device based on the corresponding identification information of the user. For example, the personal communication device 100 may have an application installed therein that manages the identification information of the user and receives the usage information. In this case, an account by which the user logs in this application may match the user's identification information in one to one manner. In this way, the use of the brain stimulating device 200 may be restricted based on each account.

Because the usage authorization is assigned based on whether the identification information matches the account, the brain stimulating device 200 that may be used may be limited based on each account. In this case, the server 300 may include identification information of the brain stimulating device 200 that may be used into the usage information, and transmit the usage information in operation S15.

When a plurality of the users logs in to the above-described application, each above-described usage information may be allocated to each logging-in user. For example, persons A, B, and C may log in the application installed on the same personal communication device 100 using different accounts acc_A, acc_B, and acc_C respectively. In one example, this situation may include a case where family members share the same tablet computer in a residential community, but create different accounts.

In this case, the application may send identification information of the logging-in users. In one embodiment, when the person A logs into the same personal communication device 100 using the account acc_A, the personal communication device 100 may send "A" as identification information of the user to the server 300 and then may receive usage information of "A" from the server 300 and may send payment information to the server 300. Subsequently, the personal communication device 100 may use the received usage information and payment information of "A" only when the user logs in the application using the same acc_A.

In this case, usage information and payment information of users who do not log in the application may be stored in the personal communication device 100. However, the use and payment information of the user who does not log in the application is not available to other users. That is, when the person A logs in the application using the account acc_A, the usage information and payment information of only "A" may be available to the person A.

FIG. 3 shows usage information according to an embodiment of the present disclosure. A table 51 in FIG. 3 indicates that three usage information are allocated to single user identification information. In more detail, usage_id refers to identification information of usage information is assigned to individual usage information. user_id refers to identification information of a user. start_date_time and end_date_time respectively refer to a start time and an end time at which the user may start and end using the brain stimulating device 200 based on the usage information respectively. A medical staff may identify a body state of a user and may configure the usage information for using the brain stimulating device 200 based on the identified state. Alternatively, the server 300 may automatically generate the usage information based on past use records of the brain stimulating device 200. As indicated by the table 51, each of start_date_time and end_date_time may be composed of a date and a time.

machine_id refers to identification information of the brain stimulating device 200 to be used by the user. When the brain stimulating device 200 is of various types, or is placed at various locations, the server 300 may store identification information of the brain stimulating device 200. Further, machine_id may indicate a type of several brain stimulating devices 200. For example, the brain stimulating device of a type A or the brain stimulating device of a type B may be indicated by machine_id. Identification information of a plurality of brain stimulating devices 200 may be stored therein. In this case, the user may select one thereof. usage_min refers to a use time duration of the brain stimulating device 200 and indicates predefined time duration information such as 10 minutes/15 minutes/20 minutes. In another embodiment, the use time duration may be configured in an unit of a second or a unit of a hour.

usage_mode means a specific mode of the brain stimulating device 200 to be used by the user. The mode refers to a mode suitable for the user including various factors such as an intensity, a frequency, or a wavelength of electric or magnetic energy. Identification information of a function mode having an abbreviated meaning that the user can not identify may be stored in usage_mode. "price" refer to information about an economic price to be paid for the user to use the brain stimulating device. In one embodiment, "price" may indicate a card payment amount or an account transfer amount. In another embodiment, "price" may indicate a type of a coupon, points, etc. that the user pre-purchased or that has been pre-issued to the user.

A table 52 in FIG. 3 excludes the user identification information and indicates that a single user is assigned single usage information indicating that use of the device 200 may be repeated three times. The same fields as those in the table 51 are the same as described above. usage_count refers to the number of use times at which the user may use the brain stimulating device 200. In one example, the user may use the device 200 for 20 minutes each time (usage_min) in alpha_2 mode. The table 52 indicates that the user should use the device 200 all three times within a duration between start_date_time and end_date_time.

FIG. 4 shows a configuration of a time token according to an embodiment of the present disclosure.

The time token may be combined with the user's identification information and may be stored in a tuple form. The present disclosure is not limited thereto.

The time token may include information indicating that the user may use a specific brain stimulating device 200. In one embodiment, the time token may include some of the usage information 51 and 52 of FIG. 3 and may be stored in an encrypted form. Tables 61 and 62 in FIG. 4 show the time tokens associated with the usage information shown in the tables 51 and 52 of FIG. 3, respectively. The time token may be used in an encrypted manner. The time token in FIG. 4 may be stored on the personal communication device 100 and the server 300 along with the identification information user_id of the user. When the user carries the personal communication device 100 and accesses the brain stimulating device 200, the personal communication device 100 and/or the server 300 may verify the time token and allow or disallow the user to use the brain stimulating device 200 based on the verification. The time token and the user ID may be stored in a <user_id, time_token>manner In the embodiments of FIG. 3 and FIG. 4, the server may combine the time token with user_id, usage_id, and machine_id and include a stimulus state field into the time token to check validity of the time token. One embodiment of the stimulus state field may be a stimulus state indication or a stimulus available time duration (start_date_time, end_date_time), or an incentive (a price) corresponding to the stimulus.

The stimulus state indication may be configured to count down a stimulus time as shown as in usage_min in FIG. 4. Further, when a stimulation procedure is completed, 0 may be allocated to usage_min to inform that the stimulation procedure is completed. The stimulus time countdown may be performed in an unit of a minute or a second. Further, the stimulus time countdown may be stored in a form of money or points, as shown in the price field in FIG. 3.

The process in accordance with the present disclosure will be described in more details.

FIG. 5 illustrates a process of using the brain stimulating device 200 using a time token according to an embodiment of the present disclosure.

The user carries the personal communication device 100 and accesses the brain stimulating device 200. In one embodiment, the user may mount the brain stimulating device 200 to the head thereof. The brain stimulating device 200 may be placed in a specific space or an individual may carry the device 200 in a portable way. When the personal communication device 100 identifies that the user accesses the brain stimulating device 200, the personal communication device 100 identifies the corresponding brain stimulating device 200 S510, and identifies the time token previously stored therein to check whether the user may use the device 200 S511. The personal communication device 100 sends the time token that may be used by the corresponding brain stimulating device 200 to the server 300 S513. In this process, the user identification information may be transmitted together with the time token. In addition, identification information of the brain stimulating device 200 as accessed by the user may be transmitted to the server 300.

The server 300 confirms whether the transmitted time token is valid S515. When the time token is valid, the server sends the time token to the brain stimulating device 200 scheduled to be used by the user S520. In this connection, the transmitted time token may be transmitted in an encrypted manner which both the brain stimulating device 200 and the server 300 should comply with.

The brain stimulating device 200 may perform an operation using the received time token, and may operate according to the detailed information defined in the time token S521. For example, when a time token corresponding to usage005 shown in FIG. 4 is transmitted in S520, the brain stimulating device 200 operates in alpha_2 mode for 20 minutes. The operation may be started by the user pressing a specific button on the brain stimulating device 200. When the user presses a stop button on the brain stimulating device 200 during the operation, the brain stimulating device 200 may determine whether an operation defined in the corresponding time token is completed or is not completed based on an operation time duration up to a current time and a total use time duration.

When, based on the detailed information defined in the time token, the use of the brain stimulating device 200, i.e., a process of providing stimulation to the brain of the user ends, the brain stimulating device 200 notifies the server 300 that the operation indicated by the corresponding time token has successfully completed S523. The server 300 deletes the time token S525 because the operation indicated by the previously stored time token is completed. Optionally, the server 300 instructs the personal communication device 100 to delete the time token S527. In this connection, in one example, deleting may include removing the time token from the personal communication device 100. Further, in another embodiment, the deletion includes changing a value of the time token to indicate that the time token is no longer available or has expired on the personal communication device 100, or deactivating the time token to indicate that the time token has expired. Therefore, deleting the time token stored in the personal communication device 100 herein includes various embodiments of changing or deleting a value of a specific field of the time token so that the user may no longer use the brain stimulating device 200 based on the corresponding time token.

The personal communication device 100 deletes an indicated time token S529. The user may then use the brain stimulating device 200 based on a different time token.

In one example, when, unlike operation S520, the brain stimulating device 200 does not receive the time token, the device 200 does not operate. This is a case where the user is not allowed by the server 300 to use the device 200. Alternatively, this is a case where a type or identification information of a brain stimulating device indicated by a time token purchased by the user is different from a type or identification information of a brain stimulating device 200 actually mounted to the user.

FIG. 6 shows a process of using the brain stimulating device 200 using a time token according to another embodiment of the present disclosure. Unlike FIG. 5, FIG. 6 shows a process in which the brain stimulating device 200 receives a time token from the personal communication device 100 and sends the time token to the server 300 to verify the token.

The user carries the personal communication device 100 and accesses the brain stimulating device 200. In one embodiment, the user may mount the brain stimulating device 200 to a her/his head. The brain stimulating device 200 may be placed in a specific space. Alternatively, an individual may carry the device 200 in a portable way. When the personal communication device 100 identifies that the user accesses the brain stimulating device 200, the stored time token is transmitted to the brain stimulating device 200 S610. In this connection, the personal communication device 100 may identify identification information of the brain stimulating device 200 and transmit a corresponding time token thereto to the brain stimulating device 200. Alternatively, the personal communication device 100 may determine a currently available time token using current time information and send the same to the brain stimulating device 200.

The brain stimulating device 200 verifies whether the received time token is suitable for use S611. To this end, the machine_id included in the time token may be verified by the device 200 or time information contained in the time token may be verified by the device 200. Thereafter, the brain stimulating device 200 transmits the first verified time token to the server 300 S613. In this process, the user identification information may be transmitted together with the time token. In addition, the identification information of the brain stimulating device 200 may be transmitted to the server 300.

The server 300 confirms whether the transmitted time token is valid S615. When the result indicates that the time token is valid, the server 300 notifies the brain stimulating device 200 scheduled to be used by the user that the validity has been confirmed S620. In one example, notifying includes sending a notification message. Further, the notification message may include identification information of the time token whose validity is identified. Further, the notification message may be sent in an encrypted manner which both of the brain stimulating device 200 and the server 300 should comply with.

The brain stimulating device 200 may perform an operation using the time token whose validity is confirmed, and may operate according to the detailed information defined in the time token S621. For example, when a validity of a time token corresponding to usage005 in FIG. 4 is confirmed, the brain stimulating device 200 operates in alpha_2 mode for 20 minutes.

The operation of the device 200 may be started by the user pressing a specific button on the brain stimulating device 200. When the user presses a stop button on the brain stimulating device 200 during the operation, the brain stimulating device 200 may determine whether the operation defined in the corresponding time token is completed or is not completed, based on an operation time duration up to a current time, and a total use time duration.

When, based on the detailed information defined in the time token, the use of the brain stimulating device 200, i.e., a process of providing stimulation to the brain of the user ends, the brain stimulating device 200 notifies the server 300 that the operation indicated by the corresponding time token has completed successfully S623. Further, the brain stimulating device 200 informs the personal communication device 100 that the operation indicated by the corresponding time token has successfully completed S624. The server 300 and the personal communication device 100 delete the time token which indicates the operation as completed based on the received notification S625 and S626. In this connection, deleting means deleting the time token stored in the personal communication device 100 as described above with reference to FIG. 5. The deletion includes various embodiments of changing or deleting a value of a specific field of a time token so that the user may no longer use the brain stimulating device 200 based on the corresponding time token.

In the above-described process, the personal communication device 100 and the brain stimulating device 200 allow the user to perform an operation of the brain stimulating device 200 including a predetermined procedure. In one example, when a use amount of the brain stimulating device 200 increases, a corresponding incentive may be provided to the user. Further, the personal communication device 100 may indicate a use alarm to the user based on the usage information in FIG. 3 or the time token in FIG. 4 to encourage the user to use the brain stimulating device 200. This will be described in more details.

FIG. 7 shows that the usage information is updated after an operation of the brain stimulating device according to an embodiment of the present disclosure. A time token is generated based on usage005 in the usage information of the table 51 of FIG. 3. Then, the procedure of FIG. 5 or FIG. 6 is executed using the generated time token. Thus, a user corresponding to an identifier user0001 uses the brain stimulating device 200. Then, the server 300 updates the usage information. In one embodiment, it may be indicated that the previously stored usage information may be used. The usage005 as used may be indicated as "use completed" in the price field. This may correspond to a table 71. The usage information may be provided to the personal communication device 100 from the server 300.

Next, upon using the usage005, the incentive may be provided to the user and, accordingly, the price may be adjusted. This corresponds to a table 72. It may be seen based on the previous table 51 that a price of usage006 changes from 25000 to 23000. Further, the usage 005 as used may be indicated as "use completed" in the price field.

In another embodiment, upon using the usage005, usage information to be subsequently used by the user may be changed. This corresponds to a table 73. It may be seen that usage_mode of, for example, usage006 changes from alpha_1 to alpha_2. In this connection, in one embodiment, the server 300 receives state information of the user acquired during the operation of the brain stimulating device 200 according to the usage 005 from the brain stimulating device 200 and reads the state information, and then, change the usage_mode to a usage mode appropriate for the state of the user.

In one example, the user may receive a notification message such that the user sufficiently use the brain stimulating device 200 for a predetermined duration indicated by the usage information as purchased by the user or as allocated thereto.

FIG. 8 illustrates a notification message of a personal communication device according to an embodiment of the present disclosure. When an end time end_date_time of use or procedure defined in the usage information of the table 51 of FIG. 3 reaches an end time of a predefined duration (for example, 3 days), a personal communication device 100a may output a message 81 such that the user performs the procedure. In this connection, when the user has not paid for corresponding usage information (usage_id being usage005), the personal communication device 100a may display a payment button on the display to encourage the payment and the use of the brain stimulating device 200. Alternatively, an extending button may be displayed on the display so that the user may extend the end time.

FIG. 9 shows a notification message of a personal communication device according to another embodiment of the present disclosure. Unlike FIG. 8, FIG. 9 shows a case where the user has already paid a price related to corresponding usage information (usage_id being usage005), that is, has completed the payment. In this case, when the time token is stored on the personal communication device 100 but the end time end_date_time of the use time duration reaches an end time of a predefined duration (for example 3 days), a personal communication device 100a may output a message 91 such that the user performs the procedure. In this connection, when the user has not reserved use related to the corresponding usage information (usage_id being usage005), the personal communication device 100a may display a reservation button to encourage the use of the brain stimulating device 200. Alternatively, the extending button may be displayed so that the user may extend the end time.

Figure 10:
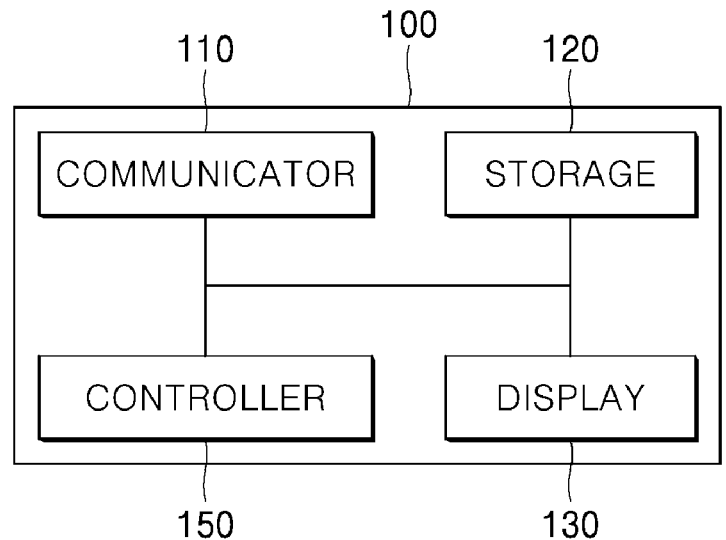
FIG. 10 shows a configuration of a personal communication device according to one embodiment of the present disclosure.

FIG. 10 shows a configuration of a personal communication device according to one embodiment of the present disclosure.

The personal communication device 100 includes a communicator 110, a storage 120, a display 130, and a controller 150.

The communicator 110 communicates with the server 300 and the brain stimulating device 200. In more detail, the identification information of the user may be transmitted by the communicator 110. The communicator 110 may send and receive the time token. After the brain stimulating device 200 is used by the user based on the usage authority defined in the time token, the communicator 110 receives the message to delete or deactivate the time token.

As described above in the embodiments of FIG. 2, FIG. 5 and FIG. 6, the personal communication device 100 operates as follows.

First, as shown in FIG. 2, in a process of storing the time token, the communicator 110 may perform the operation S11 to transmit the identification information of the user to the server 300, and the communicator 110 may receive the time token having the usage authorization of the brain stimulating device 200 configured therein, from the server 300 and may store the time token in the storage 120 of the personal communication device 100 (operation S37). In this process, as shown in S13 to S21 of FIG. 2, the controller 150 may generate payment information required to receive the time token from the server 300 and control the communicator 110 to transmit the payment information to the server 300.

In one example, after the time token is stored in the storage 120 of the personal communication device 100, the user carrying the personal communication device 100 accesses the brain stimulating device 200. In response to the access, the communicator 110 identifies an adjacent brain stimulating device 200 thereto and transmits the stored time token to the adjacent brain stimulating device 200 (S610 in FIG. 6) or to the server 300 (S513 in FIG. 5).

The server 300 identifies whether the time token received directly from the personal communication device 100 or indirectly from the brain stimulating device 200 is valid. When the time token is valid, the server 300 may allow the brain stimulating device 200 to operate. As a result, the brain stimulating device 200 operates in response to the configured time token, and then, a process of deleting or deactivating the time token is performed.

More specifically, after a time duration corresponding to the use time duration of the brain stimulating device 200 stored in the time token has lapsed, the communicator 110 of the personal communication device 100 may receive a message to delete the time token or to change the value of the specific field to deactivate the time token, from the brain stimulating device 200 or the server 300 (S527 in FIG. 5 or S624 in FIG. 6). Accordingly, the controller 150 proceeds to deactivate the time token or delete the time token (S529 in FIG. 5 or S626 in FIG. 6).

In the above process of S11 to S37 in FIG. 2, the communicator 110 may receive the usage information of the brain stimulating device 200 from the server 300 (S15 in FIG. 2). As described above, after the brain stimulating device operates based on the time token, contents of the usage information may change based on the deleting or deactivating of the time token. This has been illustrated in FIG. 7. In one example, the tables in FIG. 7 may be output on the display of the personal communication device 100. The table 71 may correspond to the display of the usage information of the table 51 in FIG. 3 on the personal communication device 100.

The change of the usage information may mean a state change of the usage information, a change of the payment price of other usage information, or a change of the mode or the time of other usage information.

Further, when the usage information or the time token is not used, the display 130 may output the predetermined message as shown in FIG. 8 and FIG. 9.

In one embodiment, when a duration from a current time when the time token is not used to the end time of the time token is smaller than a predefined duration, the display 130 may output the end time of the time token to encourage the user to use the brain stimulating device.

Figure 11:
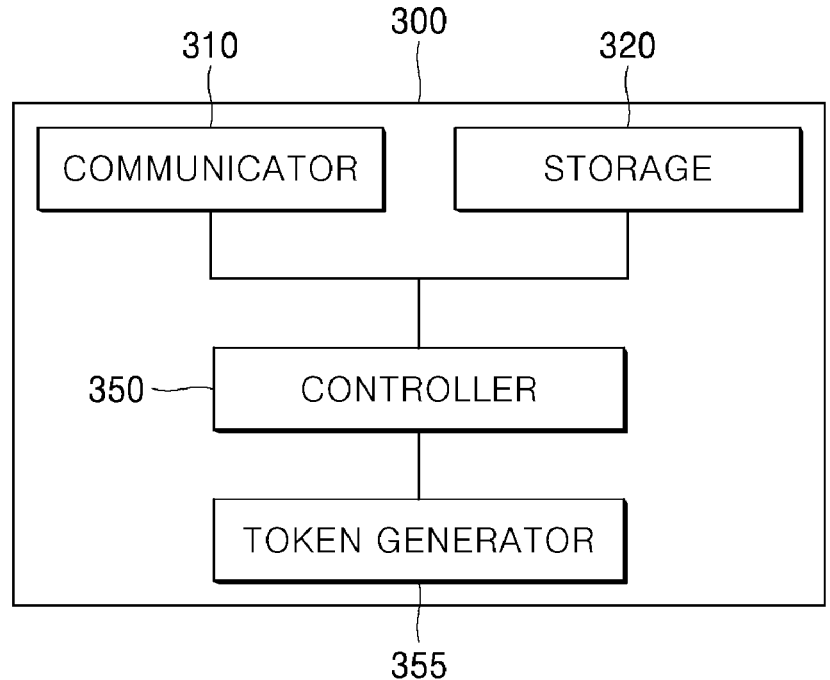
FIG. 11 shows a configuration of a server according to an embodiment of the present disclosure.

FIG. 11 shows a configuration of a server according to an embodiment of the present disclosure. The server 300 may include a communicator 310, a storage 320, and a controller 350. The controller 350 may generate the time token directly, or may include a token generator 355 that generates the time token.

The communicator 310 communicates with the personal communication device 100 and the brain stimulating device 200. More specifically, the identification information of the user is received by the communicator 310. The communicator 310 receives and sends the time token. After the brain stimulating device 200 is used based on the authority of the time token, the communicator 310 receives notification of completion of the operation based on the time token. Then, the communicator 310 transmits a message to instruct deleting or deactivating the time token stored in the personal communication device 100 to the personal communication device 100. In this process, the time tokens stored in storage 320 may be deleted or deactivated.

The process will be described in more detail.

First, as shown in FIG. 2, in the process in which the time token is generated and is sent to the personal communication device 100, the communicator 310 receives the user's identification information from the personal communication device 100 (operation S11). The controller 350 of the server 300 or the token generator 355 included in the controller 350 generates the time token having the usage authorization of the brain stimulating device configured therein corresponding to the identification information (S31 in FIG. 2), and stores the generated time token in the storage 320 (S33 in FIG. 2). Thereafter, the communicator 310 transmits the generated time token to the personal communication device 100 (S35 in FIG. 2) so that the time token is stored in the storage 120 of the personal communication device.

In this process, the controller 350 and the communicator 310 may receive the payment information required to generate the time token from the personal communication device 100, as shown in S13 to S21 of FIG. 2. The payment information may be communicated between the server 300 and the personal communication device 100 in various manners. The server 300 may act as a payment server.

After the server 300 generates the time token and transmits the token to the personal communication device 100, the communicator 310 may receive the corresponding time token from the personal communication device 100 or the brain stimulating device 200. This may be variously implemented according to the embodiment of S513 of FIG. 5 or S613 of FIG. 6. The validity of the received time token is identified and then the message to notify the validity is sent to the brain stimulating device 200 (S620 in FIG. 6) or the time token confirmed as being valid is sent to the brain stimulating device 200. The brain stimulating device 200 then completes the operation according to the time and the mode defined in the time token. The communicator 310 receives a message from the brain stimulating device 200 notifying that the use of the brain stimulating device as defined in the time token is completed (S523 in FIGS. 5 and S623 in FIG. 6). Since the use of the brain stimulating device 200 according to the usage authorization configured in the time token is terminated, the time token may be changed or deleted so that the brain stimulating device 200 may no longer be used based on the time token. That is, the controller 350 deletes the time token stored in the storage 320 or change a value of a specific field of the time token to deactivate the time token (S525 of FIGS. 5 and S625 of FIG. 6).

In one example, when the use of the brain stimulating device 200 based on the time token is terminated, the server 300 may update the usage information or change the usage information and may send the updated or changed used information back to the personal communication device.

In the above process of S11 to S37 of FIG. 2, the communicator 310 may transmit the usage information of the brain stimulating device 200 to the personal communication device 100 (S15 of FIG. 2). As described above, after the brain stimulating device operates according to the time token, the controller 350 may generates the result of deleting or deactivating the time token, and thus the controller 350 may change the content of the usage information. In more detail, the usage information may be changed according to the deletion or deactivation of the time token, or the controller 350 may generate new usage information according to the deletion or deactivation of the time token and may sent the new usage information to the personal communication device 100. The display of the personal communication device 100 may then output the new and updated usage information to encourage the user to use the brain stimulating device 200 or provide the incentive to the user.

The change of the usage information may mean a state change of the usage information, a change of the payment price of other usage information, or a change of the mode or the time of other usage information.

Referring to the operation of the server of FIG. 5 in more detail, in the process in which the communicator 310 receives the time token, the communicator 310 receives the time token from the personal communication device 100 (operation S513), the controller 350 identifies the validity of the received time token (operation S515), and the communicator 310 transmits the time token confirmed as having the validity to the brain stimulating device (operation S520).

Referring to the operation of the server of FIG. 6 in more detail, in the process in which the communicator 310 receives the time token, the communicator 310 receives the time token from the brain stimulating device 200 (operation S613), the controller 350 identifies the validity of the received time token (operation S615), and the communicator 310 sends a message to the brain stimulating device 200 notifying that the validity of the time token has been confirmed (operation S620).

Figure 12:
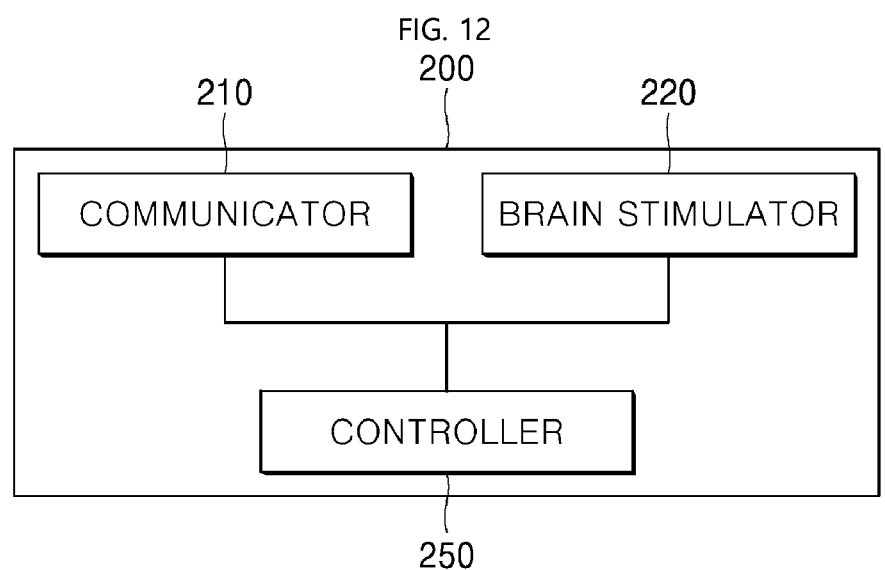
FIG. 12 shows a configuration of the brain stimulating device 200 according to an embodiment of the present disclosure.

FIG. 12 shows a configuration of the brain stimulating device 200 according to an embodiment of the present disclosure.

The brain stimulating device 200 is composed of a communicator 210, a brain stimulator 220, and a controller 250. The brain stimulator 220 provides electrical or magnetic stimulation to the brain.

The communicator 210 communicates with the server 300 or the personal communication device 100 to transmit and receive the message and the time token.

The controller 250 controls the brain stimulator 220 according to the use time and mode set in the time token. After the brain stimulator 220 operates for the use time duration set in the time token, the controller 250 generates a message to instruct deleting the time token or changing the value of the specific field of the time token to deactivate the time token. Further, the controller 250 may control the communicator 210 to transmit the aforementioned message to at least one of the server 300 or the personal communication device 100.

The brain stimulator 220 may implement at least one of various brain stimulating methods. For example, the brain stimulator 220 may implement at least one of deep electrical stimulation, transcranial magnetic stimulation, transcranial electrical stimulation, transcranial direct current stimulation, or transcranial random noise stimulation. The present disclosure is not limited to the specific brain stimulation method. Thus, the communicator 210 and the controller 250 as described above may be combined with various brain stimulating devices.

Figure 13:
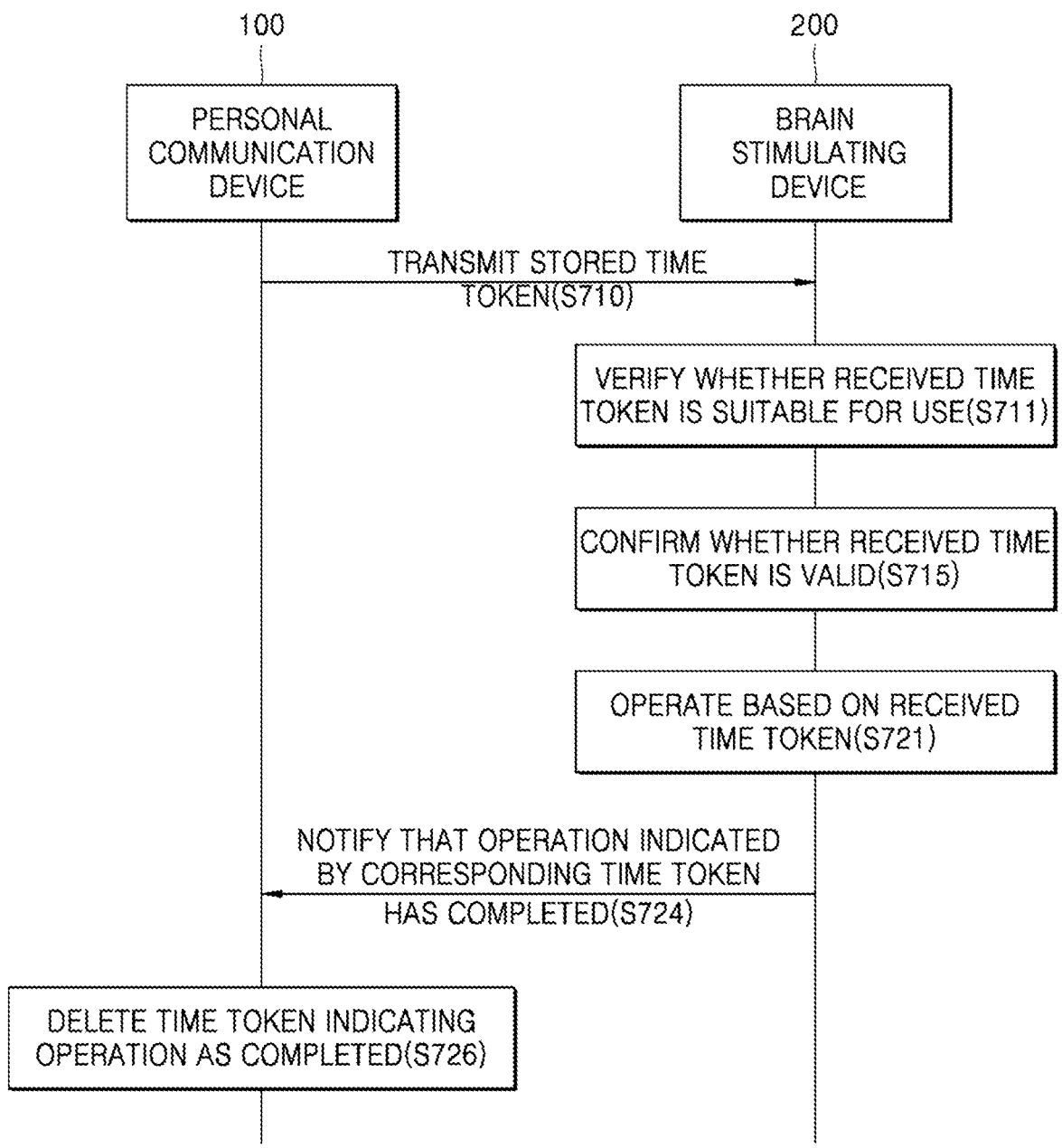
FIG. 13 shows a process of using a brain stimulating device using a time token according to another embodiment of the present disclosure.

In one embodiment, when the brain stimulating device 200 is a transcranial direct current stimulating (tDCS) device, the brain stimulator 220 may include a power supply for supplying power for electrical stimulation corresponding to a control signal applied from the controller 250, and a hydrogel patch. Further, the brain stimulator 220 may include a plurality of stimulation electrodes that receives the power supplied from the power supply to provide electrical stimulation to a living body. In one embodiment of the present disclosure, the controller 250 may control the brain stimulator 220. An turn on/off function of the power supply may be controlled in a corresponding manner to a supply amount of power or a supply or non-supply time duration of power to be applied to the stimulation electrode based on the mode set in the time token transmitted to the brain stimulating device 200, FIG. 13 shows a process of using a brain stimulating device using a time token according to another embodiment of the present disclosure. Unlike FIG. 6, FIG. 13 shows a process in which the brain stimulating device 200 receives the time token from the personal communication device 100 and directly verifies the time token. That is, the controller 250 of the brain stimulating device 200 verifies the validity of the time token transmitted from the personal communication device 100.

The user carries the personal communication device 100 and accesses the brain stimulating device 200. In one embodiment, the user may mount the brain stimulating device 200 to the head thereof. The brain stimulating device 200 may be placed in a specific space or an individual may carry the device 200 in a portable way. When the personal communication device 100 identifies that the user accesses the brain stimulating device 200, the personal communication device 100 transmits the stored time token to the brain stimulating device 200 S710. In this connection, the personal communication device 100 may identify the identification information of the brain stimulating device 200 and transmit a corresponding time token thereto to the brain stimulating device 200. Alternatively, the personal communication device 100 may determine a currently available time token based on the current time information and send the currently available time token to the brain stimulating device 200.

The brain stimulating device 200 verifies that the received time token is suitable for use S711. The brain stimulating device 200 may verify the machine_id included in the time token or the time information contained in the time token. The brain stimulating device 200 then identifies a validity of the previously-validated time token S721. The brain stimulating device 200 may integrate S711 and S715 into a single verification operation.

When the time token is identified as being valid in S715, the brain stimulating device 200 performs an operation based on the time token whose validity is confirmed. The operation may be performed according to the detailed information defined in the time token S721. For example, when the validity of the time token corresponding to usage005 in FIG. 4 is confirmed, the brain stimulating device 200 operates in alpha_2 mode for 20 minutes.

The operation may be started by the user pressing a specific button on the brain stimulating device 200. When the user presses a stop button on the brain stimulating device 200 during the operation, the brain stimulating device 200 may determine whether the operation defined in the corresponding time token is completed or is not completed based on the operation time duration up to a current time and the total use time duration.

When, based on the detailed information defined in the time token, the use of the brain stimulating device 200, i.e., a process of providing stimulation to the brain of the user ends, the brain stimulating device 200 notifies the personal communication device 100 that the operation indicated by the corresponding time token has completed successfully S724. The personal communication device 100 deletes the time token indicating the operation as completed based on the received notification S726. In this connection, deleting means deleting the time token stored in the personal communication device 100 as described above with reference to FIG. 5. The deletion includes various embodiments of changing or deleting a value of a specific field of a time token so that the user may no longer use the brain stimulating device 200 based on the corresponding time token.

In the above-described process, the personal communication device 100 and the brain stimulating device 200 allow the user to perform an operation of the brain stimulating device 200 including a predetermined procedure. In one example, when the use amount of the brain stimulating device 200 increases, the incentive may be provided to the user. Further, the personal communication device 100 may provide a use alarm to the user based on the usage information in FIG. 3 or the time token in FIG. 4 to encourage the user to use the brain stimulating device 200. This has been illustrated in FIG. 7.

When applying the present disclosure, the method may configure the usage authorization of the brain stimulating device for the user based on the time token. The server, the personal communication device, and the brain stimulating device may be implemented to support the method.

Further, in accordance with the present disclosure, the method pre-assigns the usage authorization of the brain stimulating device to the communication device of the user so that the brain stimulating device to be used by many users may safely operate based on the user identification. The brain stimulating device needs to provide a customized operation. Thus, the brain stimulating device is controlled based on the time token including information about the operation mode and information about the usage authorization rather than the brain stimulating device is directly manipulated by the user. This allows the users to use the brain stimulating device more safely.

In other words, when implementing the embodiments of the present disclosure, the brain stimulating device may operate in a user-customized manner based on the usage authorization and the user identification information.

Although a description that all of components constituting an embodiment of the present disclosure are combined into a single device or operate in a combined manner is made, the present disclosure is not necessarily limited to such an embodiment. Rather, at least one of the components may be selectively combined into a single device or may operate in a selectively combined manner within a scope of the present disclosure. Further, each of all of the components may be implemented in single independent hardware. Alternatively, some or all of the components are selectively combined to be implemented as a computer program having a program module to perform some or all functions disclosed in the present disclosure. Codes and code segments constituting the computer program may be easily inferred by those skilled in the art of the present disclosure. Such a computer program may be stored in a computer readable storage medium, and may be read and executed by a computer, thereby implementing an embodiment of the present disclosure. The storage medium of the computer program includes a storage medium including a magnetic recording medium, an optical recording medium and a semiconductor recording element. Further, the computer program embodying an embodiment of the present disclosure includes a program module transmitted in real time via an external device.

It is to be understood that the foregoing embodiments are illustrative in all respects and not restrictive. The scope of the present disclosure will be defined by the following claims rather than the foregoing detailed descriptions. Further, the meaning and scope of the claims and variations and alternatives derived from an equivalent concept thereof are to be construed as falling within the scope of the present disclosure.

What is claimed is:

1. A method for configuring a usage authorization of a brain stimulating device, the method comprising:
   transmitting, by a communicator of a personal communication device, identification information of a user to a server;
   receiving, by the communicator, usage information of the brain stimulating device from the server;
   generating, by a controller of the personal communication device, payment information required to receive a time token based on the received usage information, and controlling, by the controller, the communicator to send the payment information to the server;
   receiving, by the communicator, the time token having a usage authorization of the brain stimulating device configured therein, from the server, and, storing, by the communicator, the time token in a storage of the personal communication device;
   identifying, by the communicator, the brain stimulating device adjacent thereto, and transmitting the stored time token to the brain stimulating device or the server;
   after a time duration corresponding to a use time duration of the brain stimulating device stored in the time token has lapsed, receiving, by the communicator, a message from the brain stimulating device or the server, wherein the message instructs deleting the time token or changing a value of a specific field of the time token to deactivate the time token; and
   deactivating or deleting, by the controller, the time token based on the received message
   wherein the usage information has information on the deletion or deactivation of the time token.

2. The method of claim 1, wherein the method further comprises outputting, a display of the personal communication device, an end time of the time token when a duration from a current time at which the time token is not used to the end time of the time token is smaller than a predefined duration.

3. A method for configuring a usage authorization of a brain stimulating device, the method comprising:
   receiving, by a communicator of a server, identification information of a user from a personal communication device;
   transmitting, by the communicator, usage information of the brain stimulating device based on the received identification information to the personal communication device;
   receiving, by the communicator, payment information on the transmitted usage information from the personal communication device;
   generating, by a controller of the server, a time token having a usage authorization of the brain stimulating device based on the identification information and received payment information, and storing, by the controller, the time token in a storage of the server;
   transmitting, by the communicator, the time token to the personal communication device;
   receiving, by the communicator, the time token from the personal communication device or the brain stimulating device, and, identifying, by the controller, validity of the time token;

receiving, by the communicator, a message from the brain stimulating device to notify that use of the brain stimulating device defined in the time token is completed; and deleting, by the controller, the time token stored in the storage or changing, by the controller, a value of a specific field of the time token to deactivate the time token.

4. The method of claim 3, wherein the method further comprises:

changing, by the controller, the usage information based on the deletion or deactivation of the time token; or generating, by the controller, new usage information based on the deletion or deactivation of the time token, and transmitting, by the communicator, the new usage information to the personal communication device.

5. The method of claim 3, wherein receiving, by the communicator, the time token further includes:

receiving, by the communicator, the time token from the personal communication device;

identifying, by the controller, validity of the received time token; and transmitting, by the communicator, the identified time token whose validity is confirmed to the brain stimulating device.

6. The method of claim 3, wherein receiving, by the communicator, the time token further includes:

receiving, by the communicator, the time token from the personal communication device;

identifying, by the controller, validity of the received time token; and transmitting, by the communicator, a message to the brain stimulating device, wherein the message notifies that the validity of the time token has been confirmed.

7. A brain stimulating device comprising:

a brain stimulator configured to apply electrical or magnetic stimulation to a brain;

a communicator configured to communicate with a server or a personal communication device to send or receive a message and a time tokens thereto and therefrom; and a controller configured to:

control the brain stimulator based on a use time and a use mode defined in the time token;

after the brain stimulator has operated for a use time duration defined in the time token, generate a message to instructs deleting the time token or changing a value of a specific field of the time token to deactivate the time token; and control the communicator to transmit the message to at least one of the server or the personal communication device, wherein the brain stimulating device is a transcranial direct current stimulating (tDCS) device, and wherein the brain stimulator has:

a power supply for supplying power for electrical stimulation corresponding to a control signal applied from the controller, a hydrogel patch, and a plurality of stimulation electrodes for receiving the power supplied from the power supply to apply electrical stimulation to a living body, and wherein the controller is configured to control a turn on/off function of the power supply in a corresponding manner to a supply amount of power or a supply or non-supply time duration of power to be applied to the stimulation electrodes based on a mode defined in the time token, and wherein the controller is configured to verify validity of the time token sent from the personal communication device.

* * * * *